(12) United States Patent
Graziano et al.

(10) Patent No.: US 7,378,504 B2
(45) Date of Patent: May 27, 2008

(54) HUMAN MONOCLONAL ANTIBODIES TO FC GAMMA RECEPTOR I (CD64)

(75) Inventors: Robert Graziano, Frenchtown, NJ (US); Karuna Sundarapandiyan, Kendall Park, NJ (US)

(73) Assignee: Medarex, Inc., Princeton, NJ (US)

( * ) Notice: Subject to any disclaimer, the term of this patent is extended or adjusted under 35 U.S.C. 154(b) by 105 days.

(21) Appl. No.: 11/145,001

(22) Filed: Jun. 3, 2005

(65) Prior Publication Data
US 2008/0095784 A1    Apr. 24, 2008

Related U.S. Application Data

(60) Provisional application No. 60/576,976, filed on Jun. 3, 2004.

(51) Int. Cl.
*C07K 16/00* (2006.01)
*C12P 21/08* (2006.01)
*C07K 1/00* (2006.01)

(52) U.S. Cl. .............. 530/387.1; 530/387.3; 530/388.1; 530/388.15; 530/388.22

(58) Field of Classification Search ............ None
See application file for complete search history.

(56) References Cited

U.S. PATENT DOCUMENTS 6,682,928 B2 * 1/2004 Keler et al. ............. 435/325
2003/0039641 A1 * 2/2003 Keler et al. ............. 424/93.21

FOREIGN PATENT DOCUMENTS

| WO | WO 94/10332 | 5/1994 |
| WO | WO 98/24884 | 6/1998 |
| WO | WO 01/14424 A2 | 3/2001 |

OTHER PUBLICATIONS

Rudikoff et al. PNAS 1982, 79 :1979-1983.*
Li et al. Biochemistry 2000. 39:6296-6309.*
Brummell et al. Biochemistry 1993, 32:1180-1187.*
Kobayaski et al. Protein Engineering 1999, 12;10:879-884.*
Burks et al. PNAS 1997, 94:412-417.*
Liu, Chunlei et al., FcγRI-Targeted Fusion Proteins Result in Efficent Presentation by Human Monocytes of Antigenic and Antagonist T Cell Epitopes, *J. Clin. Invest.*, vol. 98(9):2001-2007 (Nov. 1996).
Heijnen, Ingmar A.F.M. et al., "Antigen Targeting to Myeloid-specific Human FcγRI/CD64 Triggers Enhanced Antibody Responses in Transgenic Mice," *J. Clin. Invest.*, vol. 97(2):331-338 (Jan. 1996).
Lonberg, Nils et al., "Antigen-specific human antibodies from mice comprising four distinct genetic modifications," *Letters to Nature*, vol. 368 pp. 856-859 (Apr. 1994).
Fishwild, Dianne M. et al., "High-avidity human IgGκ monoclonal antibodies from a novel strain of minilocus transgenic mice," *Nature Biotechnology*, vol. 14, pp. 845-851 (Jul. 1996).
Wallace, Paul K. et al., "FcγRI blockade and modulation for immunotherapy," *Cancer Immunol Immunother*, vol. 45, pp. 137-141 (1997).
Wiener, E. et al., "HPA-Ia-mediated platelet interaction with monocytes in vitro: Involvement of Fcγ receptor (FcγR) classes and inhibition by humanised monoclonal anti-FcγRI H22," *European Journal of Haematology*, vol. 65, pp. 399-406 (2000).
Graziano, Robert F. et al., "Construction and Characterization of a Humanized Anti-γ-lg Receptor Type I (FcγRI) Monoclonal Antibody," *The Journal of Immunology*, vol. 455, pp. 4996-5002 (1995).

* cited by examiner

*Primary Examiner*—Maher M. Haddad
*Assistant Examiner*—Chun Dahle
(74) *Attorney, Agent, or Firm*—Lahive & Cockfield, LLP; Jane E. Remillard, Esq.

(57) ABSTRACT

The present invention provides isolated monoclonal antibodies, particularly human antibodies, that bind to CD64 with high affinity. Nucleic acid molecules encoding the antibodies of the invention, expression vectors, host cells and methods for expressing the antibodies of the invention are also provided. Immunoconjugates, bispecific molecules and pharmaceutical compositions comprising the antibodies of the invention are also provided. The invention also provides methods for treating autoimmune disorders, transplant rejection, Graft Versus Host Disease, or cancer and for enhanced presentation of antigen using conjugates of an antigen and an anti-CD64 antibody.

8 Claims, 8 Drawing Sheets

```
Anti-CD64 611VH
VH3-33
JH4
```

|     | Q | V | Q | L | V | E | S | G | G | G | V | V | Q | P | G | R | S | L |
|-----|---|---|---|---|---|---|---|---|---|---|---|---|---|---|---|---|---|---|
| 1   | CAG | GTG | CAG | CTG | GTG | GAG | TCT | GGG | GGA | GGC | GTG | GTC | CAG | CCT | GGG | AGG | TCC | CTG |

CDR 1
-------------------

|     | R | L | S | C | A | A | S | G | F | I | F | S | G | Y | G | M | H | W |
|-----|---|---|---|---|---|---|---|---|---|---|---|---|---|---|---|---|---|---|
| 55  | AGA | CTC | TCC | TGT | GCA | GCG | TCT | GGA | TTC | ATC | TTC | AGT | GGC | TAT | GGC | ATG | CAC | TGG |

CDR2
-------------------

|     | V | R | Q | A | P | G | K | G | L | E | W | V | T | V | I | W | Y | D |
|-----|---|---|---|---|---|---|---|---|---|---|---|---|---|---|---|---|---|---|
| 109 | GTC | CGC | CAG | GCT | CCA | GGC | AAG | GGG | CTG | GAG | TGG | GTG | ACA | GTT | ATA | TGG | TAT | GAT |

CDR2
---------------------------------------------------

|     | G | S | N | K | Y | Y | A | D | S | V | K | G | R | F | T | I | S | R |
|-----|---|---|---|---|---|---|---|---|---|---|---|---|---|---|---|---|---|---|
| 163 | GGA | AGT | AAT | AAA | TAC | TAT | GCA | GAC | TCC | GTG | AAG | GGC | CGA | TTC | ACC | ATC | TCC | AGA |

|     | D | N | S | K | N | T | L | Y | L | Q | M | N | S | L | R | A | E | D |
|-----|---|---|---|---|---|---|---|---|---|---|---|---|---|---|---|---|---|---|
| 217 | GAC | AAT | TCC | AAG | AAC | ACG | CTG | TAT | CTG | CAA | ATG | AAC | AGC | CTG | AGA | GCC | GAG | GAC |

CDR 3
-------------------------------------

|     | T | A | V | Y | Y | C | A | R | D | T | G | D | R | F | F | D | Y | W |
|-----|---|---|---|---|---|---|---|---|---|---|---|---|---|---|---|---|---|---|
| 271 | ACG | GCT | GTG | TAT | TAC | TGT | GCG | AGA | GAT | ACG | GGG | GAT | CGG | TTC | TTT | GAC | TAC | TGG |

|     | G | Q | G | T | L | V | T | V | S | S |
|-----|---|---|---|---|---|---|---|---|---|---|
| 325 | GGC | CAG | GGA | ACC | CTG | GTC | ACC | GTC | TCC | TCA |

Figure 1A

```
Anti-CD64 611VK
L6
JK2
```

|     |     |     |     |     |     |     |     |     |     |     |     |     |     |     |     |     |     |     |
|-----|-----|-----|-----|-----|-----|-----|-----|-----|-----|-----|-----|-----|-----|-----|-----|-----|-----|-----|
|     | E   | I   | V   | L   | T   | Q   | S   | P   | A   | T   | L   | S   | L   | S   | P   | G   | E   | R   |
| 1   | GAA | ATT | GTG | TTG | ACA | CAG | TCT | CCA | GCC | ACC | CTG | TCT | TTG | TCT | CCT | GGG | GAA | AGA |

```
                                              CDR 1
                        ------------------------------------------------
         A   T   L   S   C   R   A   S   Q   S   V   S   S   Y   L   A   W  .Y
  55    GCC ACC CTC TCC TGC AGG GCC AGT CAA AGT GTT AGC AGC TAC TTA GCC TGG TAC

CDR 2
                                                          ------------------
         Q   Q   K   P   G   Q   A   P   R   L   L   I   Y   D   A   S   S   R
 109    CAA CAG AAA CCT GGC CAG GCT CCC AGG CTC CTC ATC TAT GAT GCA TCC AGC AGG

CDR 2
        ---------
         A   T   G   I   P   A   R   F   G   G   S   G   S   G   T   D   F   T
 163    GCC ACT GGC ATC CCA GCC AGG TTC GGT GGC AGT GGG TCT GGG ACA GAC TTC ACT

CDR3
                                                                         --------
         L   T   I   S   S   L   E   P   E   D   F   A   V   Y   Y   C   Q   L
 217    CTC ACC ATC AGC AGC CTA GAG CCT GAA GAT TTT GCA GTT TAT TAC TGT CAG CTG

CDR3
        ----------------------------------------
         R   S   N   W   P   P   Y   T   F   G   Q   G   T   K   L   E   I   K
 271    CGT AGC AAC TGG CCT CCG TAC ACT TTT GGC CAG GGG ACC AAG CTG GAG ATC AAA
```

Figure 1B

Anti-CD64 611 VH region

```
                                                       CDR1
3-33 Germline: Q V Q L V E S G G G V V Q P G R S L R L S C A A S G F T F S S Y G M H W V R Q
611 VH:        - - - - - - - - - - - - - - - - - - - - - - - - - - H - - - G - - - - -
                                   CDR2
33 Germline:   A P G K G L E W V A V I W Y D G S N K Y Y A D S V K G R F T I S R D N S K N T
611 VH:        - - - - - - - - - - - T - - - - - - - - - - - - - - - - - - - - - - - -
                                                  CDR3
33 Germline:   L Y L Q M N S L R A E D T A V Y Y C A R - - - D T G D R F F D Y W G Q G T L V T V S S
611 VH:        - - - - - - - - - - - - - - - - - - - -
```

Figure 2

Anti-CD64 611 VK Region

```
                                                      CDR1
L6 germline: E I V L T Q S P A T L S L S P G E R A T L S C R A S Q S V S S Y L A
611 VK:      - - - - - - - - - - - - - - - - - - - - - - - - - - - - - - - - -

CDR2
L6 germline: W Y Q Q K P G Q A P R L L I Y D A S N R A T G I P A R F S G S G S G
611 VK:      - - - - - - - - - - - - - - - - - S - - - - - - - - - - - G - - - -

CDR3
L6 germline: T D F T L T I S S L E P E D F A V Y Y C Q Q R S N W - - - P P Y T F G Q G
611 VK:      - - - - - - - - - - - - - - - - - - - - - L - - - - - - - - - - - - - -

… # HUMAN MONOCLONAL ANTIBODIES TO FC GAMMA RECEPTOR I (CD64)

RELATED APPLICATIONS

This application claims priority to U.S. Provisional Application No. 60/576,976, filed on Jun. 3, 2004, which is incorporated herein in its entirety by this reference.

BACKGROUND OF THE INVENTION

Receptors for the Fc region of antibodies (FcR) play a coordinating role in immunity. They are expressed on various types of cells and mediate functions ranging from endocytosis, phagocytosis, antibody-dependent cell-mediated cytotoxicity (ADCC), and cytokine production, to facilitation of antigen presentation. Antigen presentation represents a process in which antigens are captured, targeted to appropriate compartments, and processed before binding to major histocompatibility complex (MHC) molecules.

Leukocyte FcR for IgG (FcγR) comprises a multigene family, divided into three classes (FcγRI, II, and III) based on differences in receptor structure, cell distribution, and affinity for IgG (Van de Winkel, et al. (1993) Immunol. Today 14:215). FcγR molecules can potently enhance antigen presentation. The type of FcγR involved has been shown to be a crucial determinant for the types of epitopes presented by the antigen-presenting cell (Amigorena, et al. (1998) J. Exp. Med. 187:505).

The human high-affinity receptor for IgG, hFcγRI (CD64), is constitutively expressed on antigen-presenting cells such as monocytes, macrophages, and dendritic cells. CD64 is a preferred trigger receptor for use in therapy because it is (1) expressed primarily on immune effector cells; (2) mediates cytotoxic activities (e.g., ADCC, phagocytosis); and (3) mediates enhanced antigen presentation of antigens targeted to them. In fact, human CD64-targeted antigens are presented efficiently both in vitro and in vivo (Liu, et al. (1996) J. Clin. Invest. 98:2001; Heijnen, et al. (1996) J. Clin. Invest. 97:331). Accordingly CD64 is a therapeutically important receptor for mediating immune functions.

SUMMARY OF THE INVENTION

The present invention provides improved immunotherapeutic agents that exploit the therapeutic capacity of human CD64, a cytotoxic trigger molecule. In particular, the invention provides isolated human monoclonal antibodies which bind to human CD64, as well as therapeutic compositions, bispecific antibodies and immunoconjugates containing such antibodies.

In a preferred embodiment, the human antibodies of the present invention are capable of modulating CD64 activity including, for example, CD64 surface expression and CD64-mediated phagocytosis. In a particular embodiment, the antibody selectively binds to and modulates human CD64, without similarly modulating other human Fc receptors, such as CD32 (FcγRII) and CD16 (FcγRIII).

In another particular embodiment of the invention, the antibody is not inhibited by human IgG (the natural ligand for human CD64), e.g., it binds to CD64 at a site different from the IgG binding site. Alternatively, the antibody can inhibit IgG binding to CD64, e.g., by binding CD64 at a site which is within or near the IgG binding site.

In one embodiment, the invention provides an isolated monoclonal antibody, or an antigen-binding portion thereof, comprising a heavy chain variable region that is the product of or derived from a human $V_H$ 3-33 gene, wherein the antibody specifically binds to human CD64. In another embodiment, the invention provides an isolated monoclonal antibody, or an antigen-binding portion thereof, comprising a light chain variable region that is the product of or derived from a human $V_K$ L6 gene, wherein the antibody specifically binds to human CD64. In a preferred embodiment, the invention provides an isolated monoclonal antibody, or an antigen-binding portion thereof, wherein the antibody comprises:

(a) a heavy chain variable region that is the product of or derived from a human $V_H$ 3-33 gene, which gene encodes an amino acid sequence as set forth in SEQ ID NO: 11; and (b) a light chain variable region that is the product of or derived from a human $V_k$ L6 gene, which gene encodes an amino acid sequence as set forth in SEQ ID NO: 12;

wherein the antibody specifically binds to human CD64.

In another aspect, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises the amino acid sequence of SEQ ID NO: 3, or conservative modifications thereof;

(b) the light chain variable region CDR3 sequence comprises the amino acid sequence of SEQ ID NO: 6, or conservative modifications thereof; and (c) the antibody specifically binds to human CD64.

In one embodiment, such an antibody can exhibit one or more of the following properties:

(i) the human antibody down-modulates CD64 surface expression;

(ii) the human antibody does not block binding of CD64 to its natural ligand (IgG);

(iii) the human antibody inhibits CD64-mediated phagocytosis; or (iv) the human antibody mediates phagocytosis of target cells in the presence of human effector cells.

In a preferred embodiment, the heavy chain variable region CDR2 sequence comprises the amino acid sequence of SEQ ID NO: 2, or conservative modifications thereof; and the light chain variable region CDR2 sequence comprises the amino acid sequence of SEQ ID NO: 5, or conservative modifications thereof. In another preferred embodiment, the heavy chain variable region CDR1 sequence comprises the amino acid sequence of SEQ ID NO: 1, or conservative modifications thereof; and the light chain variable region CDR1 sequence comprises the amino acid sequence of SEQ ID NO: 4, or conservative modifications thereof. The antibody can be, for example, a human antibody, a humanized antibody or a chimeric antibody.

In another aspect, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to the amino acid sequence of SEQ ID NO: 7;

(b) the light chain variable region comprises an amino acid sequence that is at least 80% homologous to the amino acid sequence of SEQ ID NO: 8; and (c) the antibody specifically binds to human CD64.

In one embodiment, such an antibody can exhibit one or more of the following properties:
(i) the human antibody down-modulates CD64 surface expression;
(ii) the human antibody does not block binding of CD64 to its natural ligand (IgG);
(iii) the human antibody inhibits CD64-mediated phagocytosis; or
(iv) the human antibody mediates phagocytosis of target cells in the presence of human effector cells.

The antibody can be, for example, a human antibody, a humanized antibody or a chimeric antibody.

In another aspect, the invention pertains to an isolated monoclonal antibody, or antigen binding portion thereof, comprising a heavy chain variable region comprising CDR1, CDR2, and CDR3 sequences comprising the amino acid sequences of SEQ ID NO: 1, SEQ ID NO: 2 and SEQ ID NO: 3, respectively, and a light chain variable region comprising CDR1, CDR2, and CDR3 sequences comprising the amino acid sequences of SEQ ID NO: 4, SEQ ID NO: 5 and SEQ ID NO: 6, respectively, wherein the antibody specifically binds to human CD64.

In one embodiment, such an antibody can exhibit one or more of the following properties:
(i) the human antibody down-modulates CD64 surface expression;
(ii) the human antibody does not block binding of CD64 to its natural ligand (IgG);
(iii) the human antibody inhibits CD64-mediated phagocytosis; or
(iv) the human antibody mediates phagocytosis of target cells in the presence of human effector cells.

In other preferred embodiments, the invention provides an isolated monoclonal antibody, or antigen binding portion thereof comprising:
(a) a heavy chain variable region comprising the amino acid sequence of SEQ ID NO: 7; and
(b) a light chain variable region comprising the amino acid sequence of SEQ ID NO: 8;
wherein the antibody specifically binds to human CD64.

In another aspect of the invention, antibodies, or antigen-binding portions thereof, are provided that compete for binding to CD64 with any of the aforementioned antibodies.

The antibodies of the invention can be, for example, full-length antibodies, for example of an IgG1 isotype. Alternatively, the antibodies can be antibody fragments, such as Fab or Fab'2 fragments, or single chain antibodies.

The invention also provides an immunoconjugate comprising an antibody of the invention, or antigen-binding portion thereof, linked to a therapeutic agent, such as a cytotoxin or a radioactive isotope. The invention also provides a bispecific molecule comprising an antibody, or antigen-binding portion thereof, of the invention, linked to a second functional moiety having a different binding specificity than said antibody, or antigen binding portion thereof.

In another aspect, the invention pertains to a bispecific or multispecific molecule comprising the antibody, or antigen-binding portion thereof, and a second functional moiety, having a different binding specificity than said antibody, or antigen binding portion thereof, such as another antibody or a cell receptor ligand, wherein the second functional moiety has a binding specificity to a target molecule on a tumor cell or a pathogen. In one embodiment, the bispecific or multispecific molecule induces antibody dependent cell mediated cytotoxicity (ADCC) of a cell or pathogen expressing the target molecule in the presence of effector cells. In another embodiment, the bispecific or multispecific molecule induces complement mediated killing of a cell or pathogen expressing the target molecule in the presence of complement. In a preferred embodiment, the target molecule is selected from the group consisting of anthrax antigens, botulism toxin, malaria antigens, equine encephalitis virus antigen, *Y. pestis* antigens, gastrin releasing peptide receptor antigen (GRP), mucin antigens, epidermal growth factor receptor (EGF-R), HER2/neu, HER3, HER4, CD20, CD30, PSMA, carcinoembryonic antigen (CEA), Pmel17, beta-human chorionic gonadotropin (βHCG), alpha-fetoprotein (AFP), gp100, MART1, TRP-2, melan-A, NY-ESO-1, MN (gp250) idiotype, MAGE antigens, SART antigens, Tyrosinase, Telomerase, TAG-72 antigen, MUC-1 antigens, the blood group antigens Lea, Leb, LeX, LeY, H-2, B-1, and B-2, HIV-1 gag, HIV-1 env, HIV-1 nef, HBV core, FAS, HSV-1, HSV-2, p17, HTLV, FELV, ORF2 and ORF3 antigens, protozoan-specific antigens, *Candida albicans* antigen, bacterial antigens, *Toxoplasma gondii* antigen, *Treponema pallidum* antigen, *Staphylococcus aureus* antigen, *Streptococcus hemolyticus* antigen, and *Mycobacterium tuberculsis* antigen.

Another aspect of the invention provides molecules that are useful for vaccination against diseases, including cancer, by including an antigen from disease organisms, from infected cells, from gene products of disease organisms or from cancer cells. For these purposes, the invention provides compositions that are binding agents that link the useful operative antigen to an anti-CD64 antibody of the invention, which serves as a binding determinant that directs the antigen to the immune system. In a preferred embodiment, the antigen is selected from the group consisting of a viral, a bacterial, a parasitic, an allergen, a venom, a self-antigen, a transplanted antigen, and a tumor-associated antigen, such as a tumor-associated antigen selected from the group consisting of gastrin releasing peptide receptor antigen (GRP), mucin antigens, epidermal growth factor receptor (EGF-R), HER2/neu, HER3, HER4, CD20, CD30, PSMA, carcinoembryonic antigen (CEA), Pmel17, beta-human chorionic gonadotropin (βHCG), alpha-fetoprotein (AFP), gp100, MART1, TRP-2, melan-A, NY-ESO-1, MN (gp250) idiotype, MAGE antigens, SART antigens, Tyrosinase, Telomerase, TAG-72 antigen, MUC-1 antigens, the blood group antigens $Le^a$, $Le^b$, $Le^X$, $Le^Y$, H-2, B-1, and B-2. In another aspect, the invention provides a method of inducing or enhancing presentation of an antigen to an immune cell in a subject, comprising administering to the subject the vaccine conjugate comprising an antibody of the invention, linked to an antigen.

Compositions comprising an antibody, or antigen-binding portion thereof, or immunoconjugate or bispecific molecule of the invention and a pharmaceutically acceptable carrier, are also provided.

Nucleic acid molecules encoding the antibodies, or antigen-binding portions thereof, of the invention are also encompassed by the invention, as well as expression vectors comprising such nucleic acids and host cells comprising such expression vectors. Moreover, the invention provides a transgenic mouse comprising human immunoglobulin heavy and light chain transgenes, wherein the mouse expresses an antibody of the invention, as well as hybridomas prepared from such a mouse, wherein the hybridoma produces the antibody of the invention.

In another aspect, the invention provides a method of treating or preventing a disorder involving CD64 expressing cells, such as an autoimmune disease, transplant rejection, or Graft versus Host Disease (GVHD). The method comprises administering to a subject an antibody, or antigen-binding portion thereof, of the invention, such that disorder, e.g., the autoimmune disease, transplant rejection, or Graft versus Host Disease (GVHD), is treated or prevented. The disease can be, for example, rheumatoid arthritis (RA), systemic lupus erythematosus (SLE), Systemic Sclerosis, Atopic Dermatitis, Graves' disease, Hashimoto's thyroiditis, Wegner's granulomatosis, Omen's syndrome, chronic renal failure, idiopathic thrombocytopenic purpura (ITP), inflammatory bowel disease (IBD; including Crohn's Disease, Ulcerative Colitis and Celiac's Disease), insulin dependent diabetes mellitus (IDDM), acute infectious mononucleosis, HIV, herpes virus associated diseases, multiple sclerosis (MS), hemolytic anemia, thyroiditis, stiff man syndrome, pemphigus vulgaris and myasthenia gravis (MG).

In another aspect, the invention provides a method of inhibiting CD64-mediated phagocytosis of a target cell by a cell expressing CD64, comprising contacting the cell expressing CD64 with the antibody or antibody fragment of the invention, such that the phagocytosis of the target cell is inhibited.

In another aspect, the invention provides a method of inhibiting growth of a target cell comprising contacting the cell with an effective amount of a bispecific or multispecific molecule or immunoconjugate comprising an antibody of the invention, such that growth of the cell is inhibited, wherein the bispecific or multispecific molecule or immunoconjugate binds to a component on the target cell. In one aspect, growth is inhibited by ADCC. In another aspect, growth is inhibited by complement mediated cellular cytotoxicity. In a preferred embodiment, the target cell is a cancer cell selected from the group of ovarian cancer, breast cancer, testicular cancer, prostate cancer, leukemia, and lymphoma. In other embodiments, the target cell is an immune cell, or a pathogen. Examples of such a pathogen include a bacterium, a virally-infected cell, and a parasite.

In another aspect, the invention provides a method of detecting the presence of CD64 or a cell expressing CD64 in a sample, comprising:

(a) contacting the sample with an antibody of the invention under conditions that allow for formation of a complex between the antibody and CD64; and (b) detecting the formation of the complex.

The invention also provides methods for making "second generation" anti-CD64 antibodies based on the sequences of the anti-CD64 antibodies provided herein. For example, the invention provides a method for preparing an anti-CD64 antibody comprising:

(a) providing: (i) a heavy chain variable region antibody sequence comprising CDR1, CDR2, and CDR3 sequences comprising the amino acid sequences of SEQ ID NO: 1, SEQ ID NO: 2 and SEQ ID NO: 3, respectively; and/or (ii) a light chain variable region antibody sequence comprising CDR1, CDR2, and CDR3 sequences comprising the amino acid sequences of SEQ ID NO: 4, SEQ ID NO: 5 and SEQ ID NO: 6, respectively;

(b) altering at least one amino acid residue within the heavy chain variable region antibody sequence and/or the light chain variable region antibody sequence to create at least one altered antibody sequence; and (c) expressing the altered antibody sequence as a protein.

Other features and advantages of the instant invention will be apparent from the following detailed description and examples which should not be construed as limiting.

BRIEF DESCRIPTION OF THE DRAWINGS

FIG. 1A shows the nucleotide sequence (SEQ ID NO: 9) and amino acid sequence (SEQ ID NO: 7) of the heavy chain variable region of the 611 human monoclonal antibody. The CDR1 (SEQ ID NO: 1), CDR2 (SEQ ID NO: 2) and CDR3 (SEQ ID NO: 3) regions are delineated and the V, D and J germline derivations are indicated.

FIG. 1B shows the nucleotide sequence (SEQ ID NO: 10) and amino acid sequence (SEQ ID 8) of the light chain variable region of the 611 human monoclonal antibody. The CDR1 (SEQ ID NO: 4), CDR2 (SEQ ID NO: 5) and CDR3 (SEQ ID NO: 6) regions are delineated and the V and J germline derivations are indicated.

FIG. 2 shows the alignment of the amino acid sequence of the heavy chain variable region of 611 (SEQ ID NO: 7) with the human germline $V_H$ 3-33 amino acid sequence (SEQ ID NO: 11).

FIG. 3 shows the alignment of the amino acid sequence of the light chain variable region of 611 (SEQ ID NO: 8) with the human germline $V_k$ L6 amino acid sequence (SEQ ID NO: 12).

DETAILED DESCRIPTION OF THE INVENTION

Figure 4:
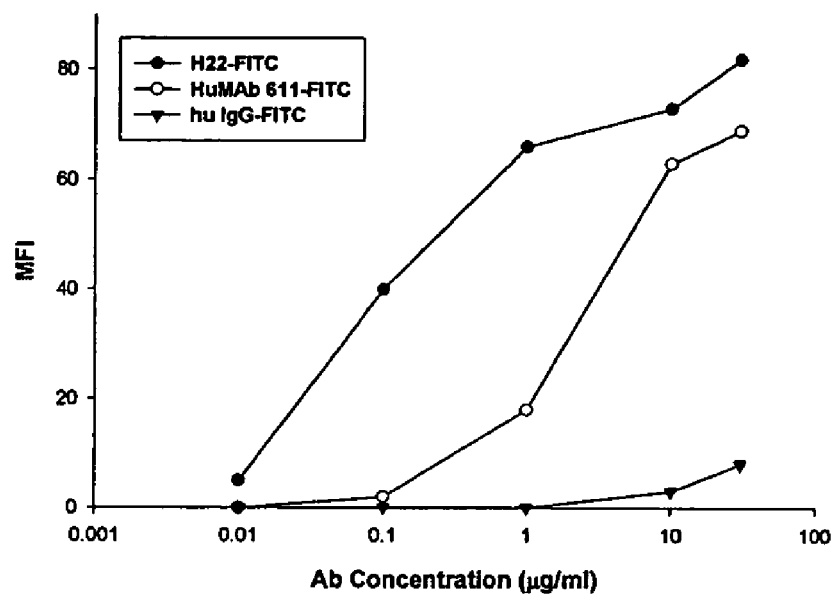
FIG. 4 is a graph showing that FITC-labeled human monoclonal antibody (HuMab) 611 binds to CD64 in the presence of human IgG, demonstrating that it binds outside the ligand binding site. The humanized anti-CD64 antibody H22 was used as a positive control and nonspecific IgG1 was used as a negative control.

The present invention provides improved antibody-based therapies and compositions for exploiting the therapeutic capacity of the human high-affinity receptor for IgG, CD64. Therapies of the invention employ isolated human monoclonal antibodies and/or related compositions containing the antibodies that bind to an epitope present on CD64. In a particular embodiment, the antibodies of the present invention selectively bind to and modulate CD64, without similarly modulating other human Fc receptors, such as CD32 (FcγRII) and CD16 (FcγRIII). For example, human antibodies of the present invention can selectively engage in (1) CD64 cross-linking, (2) down-modulation of CD64 expression, (3) blocking of CD64-mediated phagocytosis, and (4) triggering of CD64-mediated superoxide induction, without substantially engaging in the same effects with respect to CD32 or CD16.

Methods of using antibodies and antibody derivatives (e.g., conjugates and bispecifics) of the invention therapeutically (e.g., to treat and/or prevent a wide variety of diseases) and to mediate phagocytosis and/or lysis of a target cell or pathogen are also encompassed by the invention. For example, based on their ability to bind to both CD64 bearing immune cells and specific target cells (i.e., cells whose elimination would be beneficial to the host), bispecific and multispecific molecules of the present can be used to treat several diseases, such as autoimmune diseases and cancers.

In another embodiment exemplified herein, the human antibodies are produced in a nonhuman transgenic animal, e.g., a transgenic mouse, capable of producing multiple isotypes of human monoclonal antibodies to CD64 by undergoing V-D-J recombination and isotype switching. Accordingly, aspects of the invention include not only antibodies, antibody fragments, bispecific/multispecific antibodies and pharmaceutical compositions thereof, but also nonhuman transgenic animals, B-cells, transfectomas and hybridomas that produce monoclonal antibodies.

In order that the present invention may be more readily understood, certain terms will be defined as follows. Additional definitions are set forth throughout the detailed description.

As used herein, the terms "human CD64," "human high affinity IgG receptor," and "human Fc-gamma receptor I" (FcγRI) are used interchangeably and are intended to include the FcγRIa gene product located on human chromosome 1q21.1. FcγRI (CD64) is constitutively expressed on antigen-presenting cells, such as monocytes, macrophages, and dendritic cells. CD64 is a preferred trigger receptor because it is (1) expressed primarily on immune effector cells; (2) mediates cytotoxic activities (e.g., ADCC, phagocytosis); and (3) mediates enhanced antigen presentation of antigens targeted to them. Notwithstanding, human antibodies of the invention that bind to human CD64 may also bind to CD64 from other non-human species, (e.g., other mammals and vertebrates) and/or related receptors.

As used herein, the term "effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cell-mediated cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of FcαRI has been found to be up-regulated by G-CSF or GM-CSF. This enhanced expression increases the effector function of FcαRI-bearing cells against targets. An effector cell can phagocytose or lyse a target antigen or a target cell. Preferred effector cells of the invention are CD64-expressing effector cells, which include monocytes, macrophages and dendritic cells.

"Target cell" refers to any cell or pathogen whose elimination would be beneficial in a subject (e.g., a human or animal) and that can be targeted by a composition (e.g., a human monoclonal antibody, a bispecific, or a multispecific molecule) of the invention. For example, the target cell can be a cell expressing or overexpressing CD64. Alternatively, the target cell can be a tumor cell, such as a cell selected from cancer of the breast, ovary, prostate, testicle, lung, colon, rectum, pancreas, liver, central nervous system, kidney, head, neck, bone, blood, or lymphatic system. In addition, target cells include auto-antibody producing lymphocytes (for treatment of autoimmune disease) and IgE-producing lymphocytes (for treatment of allergy). Target cells further include microorganisms (e.g., a bacterium or a virally-infected cell). Microorganisms include pathogens, viruses, bacteria, fungi, and protozoa. Still other suitable targets include soluble antigens, such as rheumatoid factor and other auto-antibodies and toxins.

The term "antigen" refers to any natural or synthetic immunogenic substance, such as a protein, peptide, or hapten. The term "antigen" also includes substances that are nonimmunogenic in uncomplexed form, but are immunogenic when complexed. The term "uncomplexed" includes substances which are not linked to another molecule to form a molecular complex of the present invention. The term "complexed" includes substances that are linked to another molecule (e.g., an anti-CD64 antibody of the invention) to form a molecular complex of the present invention.

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of CD64 ligand, e.g., IgG, to CD64) are used interchangeably and encompass both partial and complete inhibition/blocking. The inhibition/blocking of IgG to CD64 preferably reduces or alters the normal level or type of effector cell functions that occurs when IgG binds to CD64 without inhibition or blocking. Inhibition and blocking are also intended to include any measurable decrease in the binding affinity of IgG to CD64 when in contact with an anti-CD64 antibody as compared to the ligand not in contact with an anti-CD64 antibody, e.g., the blocking of CD64 ligands to CD64 by at least about 10%, 20%, 30%, 40%, 50%, 60%, 70%, 80%, 90%, 99%, or 100%.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CD64). It has been shown that the antigen-binding function of an antibody can be performed by fragments of a full-length antibody.

Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "epitope" means a molecular determinant, such as a protein determinant, capable of specific binding to, or specific binding by, an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell, e.g., CD64. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as CD64, and to other targets, such as Fc receptors on effector cells.

The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

The term "human antibody derivatives" refers to any modified form of the human antibody, e.g., a conjugate of the antibody and another agent or antibody.

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor, e.g., CD64, on an effector cell, and a binding specificity for an antigen or epitope on a target cell, e.g., a tumor cell.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to refer to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that specifically binds to CD64 is substantially free of antibodies that specifically bind antigens other than CD64). An isolated antibody that specifically binds to an epitope, isoform or variant of human CD64 may, however, have cross-reactivity to other related antigens, e.g., from other species (e.g., CD64 species homologs). Moreover, an isolated antibody may be substantially free of other cellular material and/or chemicals. In one embodiment of the invention, a combination of "isolated" monoclonal antibodies having different specificities are combined in a well defined composition.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to an antibody having a $K_D$ of $10^{-8}$ M or less, more preferably $10^{-9}$ M or less and even more preferably $10^{-1}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M).

As used herein, "isotype" refers to the antibody class (e.g., IgM or IgG1) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotopic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., VH, VL, CDR3) that bind to CD64, is intended to refer to a nucleic acid molecule in which the nucleotide sequences encoding the antibody or antibody portion are free of other nucleotide sequences encoding antibodies or antibody portions that bind antigens other than CD64, which other sequences may naturally flank the nucleic acid in human genomic DNA.

As disclosed and claimed herein, the sequences set forth in SEQ ID NOs: 1-10 include "conservative sequence modifications", i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs: 1-10 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD64 antibody is preferably replaced with another amino acid residue from the same side chain family.

Alternatively, in another embodiment, mutations can be introduced randomly along all or part of a anti-CD64 antibody coding sequence, such as by saturation mutagenesis, and the resulting modified anti-CD64 antibodies can be screened for binding activity.

Accordingly, antibodies encoded by the (heavy and light chain variable region) nucleotide sequences disclosed herein (i.e., SEQ ID NOs: 9 and 10) and/or containing the (heavy and light chain variable region) amino acid sequences disclosed herein (i.e., SEQ ID NOs: 7 and 8) include substantially similar antibodies encoded by or containing similar sequences which have been conservatively modified. Further discussion as to how such substantially similar antibodies can be generated based on the sequences (i.e., heavy and light chain variable regions, or CDRs thereof) disclosed herein as SEQ ID NOs: 1-10 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells, transfectomas, and lymphocytic cells.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

The terms "transgenic, nonhuman animal" refers to a nonhuman animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-CD64 antibodies when immunized with CD64 antigen and/or cells expressing CD64. The human heavy chain transgene can be integrated into the chromosomal DNA of the mouse, as is the case for transgenic, e.g., HuMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to CD64 (e.g., IgG, IgA and/or IgE) by undergoing V-D-J recombination and isotype switching.

Various aspects of the invention are described in further detail in the following subsections.

Anti-CD64 Antibodies

The antibodies of the invention are characterized by particular functional features or properties of the antibodies. For example, the antibodies bind specifically to human CD64. Preferably, an antibody of the invention binds to CD64 with high affinity, for example with a $K_D$ of $10^{-8}$ M or less or $10^{-9}$ M or less or even $10^{-10}$ M or less. In addition, the antibodies of the invention may be characterized by one or more of the following characteristics: the antibody downmodulates CD64 surface expression, the antibody inhibits CD64-mediated phagocytosis, or the antibody does not block the binding of CD64 to its natural ligand (IgG), or does not block the binding of IgG to CD64.

Standard assays to evaluate the binding ability of the antibodies toward CD64 are known in the art, including for example, ELISAs, Western blots and RIAs. Suitable assays are described in detail in the Examples. The binding kinetics (e.g., binding affinity) of the antibodies also can be assessed by standard assays known in the art, such as by Biacore analysis.

Monoclonal Antibody 611

Preferred antibodies of the invention include the human monoclonal antibody 611, isolated and structurally characterized as described in Examples 1 and 2. The $V_H$ amino acid sequence of 611 is shown in SEQ ID NO: 7. The $V_L$ amino acid sequence of 611 is shown in SEQ ID NO: 8.

Accordingly, in one aspect, the invention provides an isolated monoclonal antibody, or antigen binding portion thereof comprising:

(a) a heavy chain variable region comprising the amino acid sequence of SEQ ID NO: 7; and (b) a light chain variable region comprising the amino acid sequence of SEQ ID NO: 8;

wherein the antibody specifically binds human CD64.

In another aspect, the invention provides antibodies that comprise the heavy chain and light chain CDR1s, CDR2s and CDR3s of 611, or combinations thereof. The amino acid sequences of the $V_H$ CDR1, 2 and 3 regions are shown in SEQ ID NOs: 1, 2 and 3, respectively. The amino acid sequences of the $V_L$ CDR1, 2 and 3 regions are shown in SEQ ID NOs: 4, 5 and 6, respectively. The CDR regions are delineated using the Kabat system (Kabat, E. A., et al. (1991) *Sequences of Proteins of Immunological Interest*, Fifth Edition, U.S. Department of Health and Human Services, NIH Publication No. 91-3242).

Accordingly, in another aspect, the invention provides an isolated monoclonal antibody, or antigen binding portion thereof comprising:

(a) a heavy chain variable region comprising CDR1, CDR2, and CDR3 comprising the amino acid sequences of SEQ ID NOs: 1, 2, and 3, respectively;

(b) a light chain variable region comprising CDR1, CDR2, and CDR3 comprising the amino acid sequences of SEQ ID NOs: 4, 5, and 6, respectively;

wherein the antibody specifically binds human CD64.

Antibodies that Bind to the Same Epitope as 611

In another embodiment, the invention provides antibodies that bind to the same epitope on human CD64 as the monoclonal antibody 611 (having $V_H$ and $V_L$ sequences as shown in SEQ ID NOs: 7 and 8). Such antibodies can be identified based on their ability to cross-compete with 611 in standard CD64 binding assays. The ability of a test antibody to inhibit the binding of 611 to human CD64 demonstrates that the test antibody can compete with 611 for binding to human CD64 and thus binds to the same epitope on human CD64 as 611. In a preferred embodiment, the antibody that binds to the same epitope on human CD64 as 611 is a human monoclonal antibody. Such human monoclonal antibodies can be prepared and isolated as described in the Examples.

Antibodies Having Particular Germline Sequences

In certain embodiments, an antibody of the invention comprises a heavy chain variable region from a particular germline heavy chain immunoglobulin gene and/or a light chain variable region from a particular germline light chain immunoglobulin gene.

For example, in a preferred embodiment, the invention provides an isolated monoclonal antibody, or an antigen-binding portion thereof, comprising a heavy chain variable region that is the product of or derived from a human $V_H$ 3-33 gene, wherein the antibody specifically binds to human CD64. In another preferred embodiment, the invention provides an isolated monoclonal antibody, or an antigen-binding portion thereof, comprising a light chain variable region that is the product of or derived from a human $V_k$ L6 gene, wherein the antibody specifically binds to human CD64.

In yet another preferred embodiment, the invention provides an isolated monoclonal antibody, or an antigen-binding portion thereof, wherein the antibody:

(a) comprises a heavy chain variable region that is the product of or derived from a human $V_H$ 3-33 gene (which encodes the amino acid sequence set forth in SEQ ID NO: 11);

(b) comprises a light chain variable region that is the product of or derived from a human $V_k$ L6 gene (which encode the amino acid sequences set forth in SEQ ID NOs: 12); and (c) specifically binds to human CD64.

An example of an antibody having $V_H$ and $V_K$ of VH 3-33 and Vk L6, respectively, is the 611 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins (e.g., using the Vbase database) and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention comprises heavy and light chain variable regions comprising amino acid sequences that are homologous to the amino acid sequences of the preferred antibodies described herein, and wherein the antibodies retain the desired functional properties of the anti-CD64 antibodies of the invention.

For example, the invention provides an isolated monoclonal antibody, or antigen binding portion thereof, comprising a heavy chain variable region and a light chain variable region, wherein:

(a) the heavy chain variable region comprises an amino acid sequence that is at least 80% homologous to the amino acid sequence of SEQ ID NO: 7;

(b) the light chain variable region comprises an amino acid sequence that is at least 80% homologous to the amino acid sequence of SEQ ID NO: 8; and (c) the antibody specifically binds to human CD64.

In one embodiment, such an antibody can exhibit one or more of the following properties:

(i) the human antibody down-modulates CD64 surface expression;

(ii) the human antibody does not block binding of CD64 to its natural ligand (IgG) (or does not block the binding of the natural ligand, IgG, to CD64);

(iii) the human antibody inhibits CD64-mediated phagocytosis; or (iv) the human antibody mediates phagocytosis of target cells in the presence of human effector cells.

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 7 or 8, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 11'-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., 611), or conservative modifications thereof, and wherein the antibodies retain the desired functional properties of the anti-CD64 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:
  (a) the heavy chain variable region CDR3 sequence comprises the amino acid sequence of SEQ ID NO: 3, or conservative modifications thereof;
  (b) the light chain variable region CDR3 sequence comprises the amino acid sequence of SEQ ID NO: 6, or conservative modifications thereof; and
  (c) the antibody specifically binds to human CD64.

In one embodiment, such an antibody can exhibit one or more of the following properties:
  (i) the human antibody down-modulates CD64 surface expression;
  (ii) the human antibody does not block binding of CD64 to its natural ligand (IgG) (or does not block binding of the natural ligand, IgG, to CD64);
  (iii) the human antibody inhibits CD64-mediated phagocytosis; or
  (iv) the human antibody mediates phagocytosis of target cells in the presence of human effector cells.

In a preferred embodiment, the heavy chain variable region CDR2 sequence comprises the amino acid sequence of SEQ ID NO: 2, or conservative modifications thereof; and the light chain variable region CDR2 sequence comprises the amino acid sequence of SEQ ID NO: 5, or conservative modifications thereof. In another preferred embodiment, the heavy chain variable region CDR1 sequence comprises the amino acid sequence of SEQ ID NO: 1, or conservative modifications thereof; and the light chain variable region CDR1 sequence comprises the amino acid sequence of SEQ ID NO: 4, or conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

Antibodies that Bind to the Same Epitope as Anti-CD64 Antibodies of the Invention In another embodiment, the invention provides antibodies that bind to the same epitope as do the various anti-CD64 antibodies of the invention provided herein, such as other human antibodies that bind to the same epitope as the 611 antibody described herein. Such additional antibodies can be identified based on their ability to cross-compete (e.g., to competitively inhibit the binding of, in a statistically significant manner) with other antibodies of the invention, such as 611, in standard CD64 binding assays. The ability of a test antibody to inhibit the binding of, e.g., 611 to human CD64 demonstrates that the test antibody can compete with that antibody for binding to human CD64; such an antibody may, according to non-limiting theory, bind to the same or a related (e.g., a structurally similar or spatially proximal) epitope on human CD64 as the antibody with which it competes. In a preferred embodiment, the antibody that binds to the same epitope on human CD64 as 611 is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1, CDR2, and CDR3 sequences of SEQ ID NOs: 1, 2, and 3, respectively, and a light chain variable region comprising CDR1, CDR2, and CDR3 sequences comprising an amino acid sequence of SEQ ID NOs: 4, 5, and 6, respectively. Thus, such antibodies contain the $V_H$ and $V_L$ CDR sequences of monoclonal antibody 611 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies of the invention are those that are structurally similar to the framework sequences used by selected antibodies of the invention, e.g., similar to the $V_H$ 3-33 sequence (encoding the amino acid sequence of SEQ ID NO: 11) and/or the $V_k$ L6 framework sequence (encoding the amino acid sequence of SEQ ID NO: 12) used by preferred monoclonal antibodies of the invention. The $V_H$ CDR1, 2 and 3 sequences, and the $V_K$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-CD64 monoclonal antibodies, or antigen binding portions thereof, comprising a heavy chain variable region comprising: (a) $V_H$ CDR1, CDR2, and CDR3 regions comprising the amino acid sequences of SEQ ID NOs: 1, 2, and 3, respectively, or an amino acid sequence having one, two, three, four or five amino acid substitutions, deletions or additions as compared to SEQ ID NOs: 1, 2, and 3; (b) $V_K$ CDR1, CDR2, and CDR3 regions comprising the amino acid sequences of SEQ ID NOs: 4, 5, and 6, respectively, or an amino acid sequence having one, two, three, four or five amino acid substitutions, deletions or additions as compared to SEQ ID NOs: 4, 5, and 6.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. For example, for 611, amino acid residue #28 (within FR1) of $V_H$ is an isoleucine whereas this residue in the corresponding $V_H$ 3-33 germline sequence is a threonine. As another example, for 611, amino acid residue #49 (within FR2) of $V_H$ is a threonine whereas this residue in the corresponding $V_H$ 3-33 germline sequence is an alanine. To return the framework region sequences to their germline configuration, the somatic mutations can be "backmutated" to the germline sequence by, for example, site-directed mutagenesis or PCR-mediated mutagenesis (e.g., residue 28 within FR1 of the $V_H$ of 611 can be "backmutated" from isoleucine to threonine or residue 49 within FR2 of the $V_H$ of 611 can be "backmutated" from threonine to alanine). Such "backmutated" antibodies are also intended to be encompassed by the invention.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180).

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-CD64 antibodies having $V_H$ and $V_K$ sequences disclosed herein can be used to create new anti-CD64 antibodies by modifying the $V_H$ and/or $V_K$ sequences, or the constant region(s) attached thereto. Thus, in another aspect of the invention, the structural features of an anti-CD64 antibody of the invention, e.g. 611, are used to create structurally related anti-CD64 antibodies that retain at least one functional property of the antibodies of the invention, such as binding to human CD64. For example, one or more CDR regions of 611, or mutations thereof, can be combined recombinantly with known framework regions and/or other CDRs to create additional, recombinantly-engineered, anti-CD64 antibodies of the invention, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-CD64 antibody comprising:
  (a) providing: (i) heavy chain variable region antibody sequences comprising CDR1, CDR2, and CDR3 sequences of SEQ ID NOs: 1, 2, and 3, respectively; and/or (ii) light chain variable region antibody sequences comprising CDR1, CDR2, and CDR3 sequences of SEQ ID NOs: 4, 5, and 6, respectively;
  (b) altering at least one amino acid residue within the heavy chain variable region antibody sequence and/or the light chain variable region antibody sequence to create at least one altered antibody sequence; and
  (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CD64 antibodies described herein, which functional properties include, but are not limited to:
  (i) specifically binds to human CD64;
  (ii) down-modulates CD64 surface expression;
  (iii) does not block binding of CD64 to its natural ligand (IgG);
  (iv) inhibits CD64-mediated phagocytosis;
  (iv) mediates phagocytosis of target cells in the presence of human effector cells.

The functional properties of the altered antibodies can be assessed using standard assays available in the art and/or described herein, such as those set forth in the Examples (e.g., flow cytometry, binding assays).

In certain embodiments of the methods of engineering antibodies of the invention, mutations can be introduced randomly or selectively along all or part of an anti-CD64 antibody coding sequence and the resulting modified anti-CD64 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) *Current Protocols in Molecular Biology*, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Preferred nucleic acids molecules of the invention are those encoding the VH and VL sequences of the 611 monoclonal antibody. The DNA sequence encoding the VH sequence of 611 is shown in SEQ ID NO: 9. The DNA sequence encoding the VL sequence of 611 is shown in SEQ ID NO: 10.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa or lambda constant region, but most preferably is a kappa constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of the Invention

Monoclonal antibodies (mAbs) of the present invention can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against CD64 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or K, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) International Immunology 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-CD64 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CD64 antibodies of the invention. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-CD64 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of CD64 antigen and/or recombinant CD64, or an CD64 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 µg) of CD64 antigen can be used to immunize the human Ig mice intraperitoneally.

Detailed procedures to generate fully human monoclonal antibodies to CD64 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CD64 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. A single strain of transgenic mice, or more than one strain of transgenic mice, can be used. For example, both HCo7 and HCo12 strains can be used. In addition, both HCo7 and HCo12 transgene can be bred together into a single mouse having two different human heavy chain transgenes (HCo7/HCo12).

Generation of Hybridomas Producing Human Monoclonal Antibodies of the Invention

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of the Invention

Antibodies of the invention also can be produced in a host cell transfectoma using, for example, a combination of well known recombinant DNA techniques and gene transfection methods (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In addition, or alternatively, to simply binding CD64, engineered antibodies such as those described above may be selected for their retention of other functional properties of antibodies of the invention, such as:

(a) specificity for human CD64;

(b) the ability to bind to human CD64 with a $K_D$ of $10^{-8}$ M or less;

(c) the ability to down-modulate CD64 surface expression;

(d) the ability to bind human CD64 at a site different from its natural ligand (IgG);

(e) the ability to inhibit CD64-mediated phagocytosis; and (f) the ability to mediate phagocytosis of target cells in the presence of human effector cells.

Characterization of Antibody Binding to Antigen

Antibodies of the invention can be tested for binding to CD64 by, for example, standard ELISA. Briefly, microtiter plates are coated with purified CD64 at 0.25 μg/ml in PBS, and then blocked with 5% bovine serum albumin in PBS. Dilutions of antibody (e.g., dilutions of plasma from CD64-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with CD64 immunogen. Hybridomas that bind with high avidity to CD64 are subcloned and further characterized. One clone from each hybridoma, which retains the reactivity of the parent cells (by ELISA), can be chosen for making a 5-10 vial cell bank stored at −140° C., and for antibody purification.

To purify anti-CD64 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-CD64 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using CD64 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CD64 human IgGs can be further tested for reactivity with CD64 antigen by Western blotting. Briefly, CD64 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Immunoconjugates

In another aspect, the present invention features an anti-CD64 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

Bispecific Molecules

In another aspect, the present invention features bispecific molecules comprising an anti-CD64 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, tumor specific or pathogen specific antigens, peptide or binding mimetic, such that a bispecific molecule results.

Accordingly, the present invention includes bispecific molecules comprising at least one first binding molecule having specificity for CD64 and a second binding molecule having specificity for a second target epitope. In a particular embodiment of the invention, the second binding molecule may be another antibody or antibody portion specific for a target antigen on a target cell, for example, a tumor cell or a pathogen. As an example, the second binding molecule may be an anti-Her2/Neu antibody, which binds breast cancer cells.

In another particular embodiment of the invention, the second binding molecule may be a ligand specific for a target receptor. As an example, the second binding molecule may be EGF or the receptor binding portion of epidermal growth factor (EGF), which binds EGF receptor on tumor cells. Therefore, the invention includes bispecific molecules capable of binding both to FcγRI expressing effector cells (e.g., monocytes, macrophages or dendritic cells, and to target cells. These bispecific molecules target CD64-expressing effector cells to target cells expressing a target molecule to which the bispecific molecule binds and triggers Fc receptor-mediated effector cell activities, such as phagocytosis of target-expressing cells, antibody dependent cell-mediated cytotoxicity (ADCC), cytokine release, or generation of superoxide anion.

In an embodiment of the invention in which the bispecific molecule is multispecific, the molecule can further include a third binding specificity, in addition to an anti-Fc binding specificity and an anti-CD64 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor (eg. anti-CD64 antibody of the invention) is provided by a monoclonal antibody, the binding of which is not blocked by human immunoglobulin G (IgG).

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-CD64 binding specificity and anti-target cell binding specificity, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Antibody Vaccine Conjugates

The present invention further provides a variety of therapeutic conjugates which include one or more human anti-CD64 antibodies (or fragments thereof) linked to one or more antigens, such as a tumor or viral antigen, to form a vaccine conjugate. This allows for targeting of a wide variety of antigens to CD64-expressing immune cells, particularly antigen presenting cells (APCs), to enhance processing, presentation and, ultimately, an immune response against the antigen(s).

Antibody-antigen vaccine conjugates of the invention can be made using any practical methodology, including genetically or chemically. In any case, the antibody portion of the conjugate may consist of the whole antibody or a portion of the antibody, such as the Fab fragment or single-chain Fv. In addition, more than one antigen can be added to a single antibody construct.

Genetically constructed anti-CD64 antibody-antigen conjugates (e.g., those expressed as a single recombinant fusion protein) can be made by linking the antigen of choice to the antibody at a variety of locations. For example, the antigen can be fused to the end of the $CH_3$ domain of the human antibody heavy chain. The antigen also can be fused at the hinged region of the antibody heavy chain in Fab-fusion constructs, or in sequence with the variable light and heavy chains ($V_H$ and $V_L$) in single chain fusion constructs (ScFv constructs). Alternatively, the antigen can be fused to the antibody light chain instead of the antibody heavy chain.

Chemically constructed antibody-antigen conjugates can be made using a variety of well known and readily available cross-linking reagents. These cross-linking reagents can be homofunctional or heterofunctional compounds, such as SPDP, SATA, SMCC, DTNB, that form covalent linkages with different reactive amino acid or carbohydrate side chains on the anti-CD64 antibody and selected antigen.

Any antigen that can be cloned and expressed or purified can be selected for use in the antibody-antigen vaccine conjugates of the present invention. Techniques for obtaining such antigens are well-known in the art. For example, tumor-associated antigens can be directly purified from cancer cells and identified by physiochemical techniques such as tandem mass spectrometry. Alternatively, tumor-specific T-cell clones can be tested against antigen-negative cells that have acquired antigen by being transfected with plasmid DNA clones to isolate the clone expressing the antigen. Synthetic peptides can then be constructed to precisely identify the antigenic site or epitope.

A significant advantage of the antibody-antigen conjugates of the present invention is their ability to rapidly elicit strong immune responses from vaccines to thereby improve the efficacy of vaccination. Accordingly, infectious disease antigens and tumor antigens against which immune responses are protective or therapeutic can be conjugated to human anti-CD64 antibodies of the invention, such as antibody 611, to form highly effective vaccines. Examples of infectious disease antigens include, but are not limited to, viral proteins, bacterial proteins and carbohydrates, fungal proteins and carbohydrates.

Antibody-antigen conjugates of the invention also can be used to improve the efficacy of vaccination against infectious organisms and their toxins that may be encountered during travel or through biowarfare. Examples of such antigens include, for example, anthrax antigens, botulism toxin, malaria antigens, equine encephalitis, and Y pestis antigens. Other suitable antigens for use in the antibody-antigen conjugates of the invention include tumor-associated antigens for the prevention or treatment of cancers. Examples of tumor-associated antigens include, but are not limited to, gastrin releasing peptide receptor antigen (GRP), mucin antigens, epidermal growth factor receptor (EGF-R), HER2/neu, HER3, HER4, CD20, CD30, PSMA, carcinoembryonic antigen (CEA), Pmel17, beta-human chorionic gonadotropin (βHCG), alpha-fetoprotein (AFP), gp100, MART1, TRP-2, melan-A, NY-ESO-1, MN (gp250) idiotype, MAGE antigens, e.g. MAGE-1 and MAGE-3, SART antigens, Tyrosinase, Telomerase, TAG-72 antigen, and MUC-1 antigens. Tumor associated antigens also include the blood group antigens, for example, $Le^a$, $Le^b$, LeX, LeY, H-2, B-1, B-2 antigens. In another preferred embodiment, more than one antigen is fused to a single anti-CD64 antibody construct. For example, a MAGE antigen can be combined with other antigens such as melanin A, tyrosinase, and gp100 along with adjuvants such as GM-CSF or IL-12, and fused to an anti-CD64 antibody construct, e.g., 611.

Other suitable antigens include viral antigens for the prevention or treatment of viral diseases. Examples of viral antigens include, but are not limited to, HIV-1 gag, HIV-1 env, HIV-1 nef, HBV core, FAS, HSV-1, HSV-2, p17, HTLV, FELV, ORF2 and ORF3 antigens. In another preferred embodiment, the selected antigen is a melanoma-specific antigen including, but not limited to, gp100 or Pmel17. In another preferred embodiment, the selected antigen is a protozoan-specific antigen, for example, a fungal antigen (e.g., *Candida albicans*). In yet another embodiment, the selected antigen is a bacterial antigen including, but not limited to, *Toxoplasma gondii* or *Treponema pallidum*. The antibody-bacterial antigen conjugates of the invention can be in the treatment or prevention of various bacterial diseases such as Anthrax, Botulism, Tetanus, *Chlamydia, Cholera, Diphtheria*, Lyme Disease, Syphilis and Tuberculosis (e.g., *Staphylococcus aureus, Streptococcus hemolyticus*, and *Mycobacterium tuberculsis*).

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-CD64 antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CD64 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD64 antibody of the invention preferably results in a decrease in severity of disease symptoms, an increase in frequency and duration of disease symptom-free periods, or a prevention of impairment or disability due to the disease affliction. For example, for the treatment of cancerous tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods of the Invention

The human antibodies, antibody compositions and methods of the present invention have numerous in vitro and in vivo diagnostic and therapeutic utilities involving the diagnosis and treatment of CD64 mediated disorders. For example, these molecules can be administered to cells in culture, e.g. in vitro or ex vivo, or to human subjects, e.g., in vivo, to treat, prevent and to diagnose a variety of disorders. As used herein, the term "subject" is intended to include human and non-human animals. Non-human animals includes all vertebrates, e.g., mammals and non-mammals, such as non-human primates, sheep, dogs, cats, cows, horses, chickens, amphibians, and reptiles. When antibodies to CD64 are administered together with another agent, the two can be administered in either order or simultaneously.

Suitable routes of administering the antibody compositions (e.g. human monoclonal antibodies, multispecific and bispecific molecules, immunoconjugates or vaccines) of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Detection Methods

In one embodiment, the antibodies (e.g., human monoclonal antibodies, multispecific and bispecific molecules, and compositions) of the invention can be used to detect levels of CD64, or levels of cells which contain CD64 on their membrane surface, which levels can then be linked to diagnosis of certain diseases. This can be achieved, for example, by contacting a sample (such as an in vitro sample) and a control sample with the anti-CD64 antibody under conditions that allow for the formation of a complex between the antibody and CD64. Any complexes formed between the antibody and CD64 are detected and compared in the sample and the control. For example, standard detection methods, well-known in the art, such as ELISA and flow cytometic assays, can be performed using the compositions of the invention.

Accordingly, in one aspect, the invention further provides methods for detecting the presence of CD64 (e.g., human CD64 antigen) in a sample, or measuring the amount of CD64, comprising contacting the sample, and a control sample, with an antibody of the invention, or an antigen binding portion thereof, which specifically binds to CD64, under conditions that allow for formation of a complex between the antibody or portion thereof and CD64. The formation of a complex is then detected, wherein a difference in complex formation between the sample compared to the control sample is indicative of the presence of CD64 in the sample.

In still another embodiment, the invention provides a method for detecting the presence or quantifying the amount of Fc-expressing cells in vivo or in vitro. The method comprises (i) administering to a subject a composition (e.g., a monoclonal antibody or a multi- or bispecific molecule) of the invention or a fragment thereof, conjugated to a detectable marker; (ii) exposing the subject to a means for detecting said detectable marker to identify areas containing Fc-expressing cells.

The compositions (e.g., human antibodies, multispecific and bispecific molecules) of the invention can also be used to target cells expressing FcγR, or CD64, for example for labeling such cells. For such use, the binding agent can be linked to a molecule that can be detected. Thus, the invention provides methods for localizing ex vivo or in vitro cells expressing Fc receptors, such as FcγR, or CD64. The detectable label can be, e.g., a radioisotope, a fluorescent compound, an enzyme, or an enzyme co-factor.

Uses of anti-CD64 Antibodies

The antibodies can be used to inhibit or block CD64 function which, in turn, can be linked to the prevention or amelioration of certain disease symptoms, thereby implicating CD64 as a mediator of the disease. Differences in CD64 expression during a disease state as compared to a non-disease state can be determined by contacting a test sample from a subject suffering from the disease and a control sample with the anti-CD64 antibody under conditions that allow for the formation of a complex between the antibody and CD64. Any complexes formed between the antibody and CD64 are detected and compared in the sample and the control.

In one embodiment, human antibodies, or binding portions thereof, of the present invention can be used to modulate CD64 levels on effector cells, such as by capping and eliminating receptors on the cell surface. Mixtures of anti-Fc receptor antibodies can also be used for this purpose.

In a preferred embodiment, anti-CD64 antibodies can be used to treat immune thrombocytopenia purpura (ITP). ITP is an autoimmune disease characterized by autoantibody-mediated destruction of IgG associated platelets (Crow A R and Lazarus A H (2003) *J pediatr Hematol Oncol* 25 Suppl 1:S14-18). Anti-CD64 antibodies bind Fc-gamma receptor, and block the Fc-gamma receptor mediated phagocytosis, prolonging the lifespan of platelets by inhibiting binding of platelets to monocytes (Wallace P K et al. (1997) *Cancer Immunol Immunother* 45:137-41; Wiener E et al. (2000) *Eur J Haematol* 65:399-406).

Uses of Bispecific and Multispecific Reagents

Further within the scope of the invention are methods for treating a disorder, such as an autoimmune disorder, a cancer, or a pathogenic infection, with the bispecific and multispecific human antibodies described above. Such bispecific and multispecific molecules include at least one binding specificity for CD64 (eg. a human anti-CD64 antibody of the present invention) and at least one binding specificity for a target antigen. In another embodiment, the antibody includes a third binding specificity for an antigen binding region to a different epitope of the same target antigen and/or receptor. Methods for eliminating unwanted cells, i.e., target cells, or antigen in a subject includes treating the subject with the bispecific or multispecific molecules of the invention. In one embodiment, such methods include administering a bispecific or multispecific molecule of the invention to a subject in which removal of target cells is desired (eg. a tumor bearing subject). In another embodiment, such methods include obtaining an aliquot of a sample of blood or blood cells from a subject, treating the blood or blood cells ex vivo with a therapeutically effective dose of a bispecific or multispecific antibody of the invention in a pharmaceutically acceptable carrier, and returning the treated blood or blood cells to the subject. Preferably, the cells of the sample of blood are isolated and expanded in culture and, more preferably, the cells of the sample of blood are treated with agents that enhance the number or activity of CD64. Such agents include cytokines, lymphokines, or growth factors, e.g., G-CSF, GM-CSF, IFN-γ, TNF, and interleukins such as IL-2, IL-10, and IL-12.

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing the target of interest, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-CD64 antibodies linked to anti-Fc-gamma RI or anti-CD3 may be used in conjunction with IgG- or IgA-receptor specific binding agents.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions (e.g., human antibodies, multispecific and bispecific molecules and immunoconjugates) of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules and immunoconjugates) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Use of Immunoconjugates and Combination Therapy

As previously described, human anti-CD64 antibodies of the invention can be co-administered with one or other more therapeutic agents, e.g., an cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days.

In one embodiment, immunoconjugates of the invention can be used to target compounds (e.g., therapeutic agents, labels, cytotoxins, radiotoxins immunosuppressants, etc.) to cells which have CD64 cell surface receptors by linking such compounds to the antibody. Thus, the invention also provides methods for localizing ex vivo or in vitro cells expressing CD64 and CD64 ligand (e.g., with a detectable label, such as a radioisotope, a fluorescent compound, an enzyme, or an enzyme co-factor). Alternatively, the immunoconjugates can be used to kill cells which have CD64 cell surface receptors by targeting cytotoxins or radiotoxins to CD64, such as to CD64-expressing tumor cells to thereby eliminate the tumor cell, or to CD64-expressing antigen-presenting cells to thereby eliminate the APCs as a means to inhibit immune responses (eg. in autoimmune disorders).

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express CD64 can be induced to do so using lymphokine preparations. Lymphokine preparations can cause a more homogeneous expression of CD64 among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

Use of Vaccines

In a particular embodiment, the invention provides methods for stimulating an immune response against an antigen of interest by immunizing a subject against the antigen, such as a cancer antigen, an antigen found on a pathogen or a cell infected by a pathogen, using a vaccine composition of the invention. Such methods include administering to the subject in a pharmaceutically acceptable carrier a composition comprising a vaccine conjugate, which conjugate comprises an anti-CD64 antibody of the invention linked to one or more antigens of interest, such as an antigen of a pathogenic infectious organism, or an antigen of infected cells, or an antigen of a cancer cell. The vaccine compositions of the invention target the antigen to antigen presenting cells, via the binding of the anti-CD64 antibody to CD64 on antigen presenting cells, thus increasing antigen presentation in order to promote an immune response against the antigen.

Treatment of Autoimmune Diseases

The compositions can be used in vitro or in vivo to treat diseases mediated by or involving CD64, for example, diseases characterized by expression, typically overexpression, of CD64 such as autoimmune disease, including those with a combination of both humoral and cellular autoimmunity, transplantation rejection, or Graft versus Host Disease (GVHD). In one embodiment, the antibodies of the present invention may block the binding site of the natural ligand, IgG, to CD64, such that binding would decrease or prevent the binding of autoantibodies against self-antigens, thereby preventing phagocytosis of the target cell, for example, platelets in idiopathic thrombocytopenic purpura or red blood cells in anemia. The compositions can also be used to treat any diseases mediated by CD64 expressing cells, including CD64 expressing malignancies, e.g., acute leukemia, or any autoimmune diseases mediated by macrophages, activated neutrophils, dendritic cells or NK cells. Examples of such diseases include, but are not limited to, rheumatoid arthritis (RA), systemic lupus erythematosus (SLE), Systemic Sclerosis, Atopic Dermatitis, Graves' disease, Hashimoto's thyroiditis, Wegner's granulomatosis, Omen's syndrome, chronic renal failure, idiopathic thrombocytopenic purpura (ITP), inflammatory bowel disease (IBD; including Crohn's Disease, Ulcerative Colitis and Celiac's Disease), insulin dependent diabetes mellitus (IDDM), acute infectious mononucleosis, HIV, herpes virus associated diseases, multiple sclerosis (MS), hemolytic anemia, thyroiditis, stiff man syndrome, pemphigus vulgaris and myasthenia gravis (MG).

Treatment of Cancer

In another embodiment, the present invention provides a method for treating or preventing a tumorigenic disorder involving CD64 expression, e.g., Hodgkin's disease, non-Hodgkin's lymphoma, Burkitt's lymphoma, anaplastic large-cell lymphomas (ALCL), cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma and other B-cell lymphomas. The method involves administering to a subject a antibody composition of the present invention in an amount effective to treat or prevent the disorder. The antibody composition can be administered alone or along with another therapeutic agent, such as a cytotoxic or a radiotoxic agent which acts in conjunction with or synergistically with the antibody composition to treat or prevent the CD64 mediated disease.

Kits

Also within the scope of the invention are kits comprising the compositions (e.g., antibodies, human antibodies, immunoconjugates, bispecific molecules, and vaccine conjugates) of the invention and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the CD64 antigen distinct from the first human antibody). Kits typically include a label indicating the intended use of the contents of the kit. The term label includes any writing, or recorded material supplied on or with the kit, or which otherwise accompanies the kit.

The present invention is further illustrated by the following examples which should not be construed as further limiting. The contents of all references, Genbank entries, patents and published patent applications cited throughout this application, as well as the Figures and the Sequence Listing, are expressly incorporated herein by reference.

EXAMPLES

Example 1

Generation of Human Monoclonal Antibodies Against CD64

Transgenic HuMab mice

Fully human monoclonal antibodies to CD64 were prepared using the HCo7 strain of HuMab transgenic mice, which expresses human antibody genes. In this mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Furthermore, this mouse strain carries a human kappa light chain transgene, KCo5, as described in Fishwild et al. (1996) *Nature Biotechnology* 14:845-851, and a human heavy chain transgene, HCo7, as described in U.S. Pat. Nos. 5,545,806; 5,625,825; and 5,545,807.

HuMab Immunizations:

To generate fully human monoclonal antibodies to CD64, the extracellular domain of human CD64 was used as the initial immunogen in raising antibodies in the HuMab mice, followed by booster immunization intraperitoneally with U937 cells, which express native full-length CD64. General immunization schemes for HuMab mice are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen.

The immune response was monitored by retroorbital bleeds. The plasma was screened by ELISA (as described below), and mice with sufficient titers of anti-CD64 human immunoglobulin were used for fusions. Mice were boosted intravenously with antigen 3 and 2 days before sacrifice and removal of the spleen. Typically, 10-15 fusions for were performed and several dozen mice were immunized.

Selection of HuMab Mice Producing Anti-IRTA5 Antibodies:

To select HuMab mice producing antibodies that bound CD64, sera from immunized mice was tested by a modified ELISA as originally described by Fishwild, D. et al. (1996). Briefly, microtiter plates were coated with purified recombinant CD64 at 1-2 µg/ml in PBS, 50 µl/wells incubated 4° C. overnight then blocked with 200 µl/well of 5% BSA in PBS. Dilutions of plasma from CD64-immunized mice were added to each well and incubated for 1-2 hours at ambient temperature. The plates were washed with PBS/Tween and then incubated with a goat-anti-human kappa light chain polyclonal antibody conjugated with alkaline phophatase for 1 hour at room temperature. After washing, the plates were developed with pNPP substrate and analyzed by spectrophotometer at OD 415-650. Mice that developed the highest titers of anti-CD64 antibodies were used for fusions. Fusions were performed as described below and hybridoma supernatants were tested for anti-CD64 activity by ELISA.

Generation of Hybridomas Producing Human Monoclonal Antibodies to CD64:

The mouse splenocytes were isolated from the HuMab mice fused with PEG to a mouse myeloma cell line based upon standard protocols. The resulting hybridomas were then screened for the production of CD64-specific antibodies. Single cell suspensions of splenic lymphocytes from immunized mice were fused to one-fourth the number of P3×63-Ag8.653 nonsecreting mouse myeloma cells (ATCC, CRL 1580) or SP2/0 nonsecreting mouse myeloma cells (ATCC, CRL 1581) with 50% PEG (Sigma). Cells were plated at approximately $1 \times 10^5$/well in flat bottom microtiter plate, followed by about two week incubation in selective medium containing 10% fetal bovine serum, 10% P388D1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1×HAT (Sigma, CRL P-7185). After 1-2 weeks, cells were cultured in medium in which the HAT was replaced with HT. Individual wells were then screened by ELISA (described below) for human anti-CD64 monoclonal IgG antibodies. Once extensive hybridoma growth occurred, medium was monitored usually after 10-14 days. The antibody secreting hybridomas were replated, screened again and, if still positive for human IgG, anti-CD64 monoclonal antibodies were subcloned at least twice by limiting dilution. The stable subclones were then cultured in vitro to generate small amounts of antibody in tissue culture medium for characterization.

Hybridoma clone 611 was selected for further analysis.

Example 2

Structural Characterization of Human Monoclonal Antibody 611

The cDNA sequences encoding the heavy and light chain variable regions of the 611 monoclonal antibody was obtained from the 611 hybridoma using standard PCR techniques and were sequenced using standard DNA sequencing techniques.

The nucleotide and amino acid sequences of the heavy chain variable region of 611 are shown in FIG. 1A and in SEQ ID NO: 9 and 7, respectively.

The nucleotide and amino acid sequences of the light chain variable region of 611 are shown in FIG. 1B and in SEQ ID NO: 10 and 8, respectively.

Comparison of the 611 heavy chain immunoglobulin sequence to the known human germline immunoglobulin heavy chain sequences demonstrated that the 611 heavy chain utilizes a VH segment from human germline VH 3-33, an undetermined D segment, and a JH segment from human germline JH4. The alignment of the 611 VH sequence to the germline VH 3-33 sequence is shown in FIG. 2. Further analysis of the 611 VH sequence using the Kabat system of CDR region determination led to the delineation of the heavy chain CDR1, CDR2 and CD3 regions as shown in FIGS. 1A and 2, and in SEQ ID NOs: 1, 2 and 3, respectively.

Comparison of the 611 light chain immunoglobulin sequence to the known human germline immunoglobulin light chain sequences demonstrated that the 611 light chain utilizes a VL segment from human germline VK L6 and a JK segment from human germline JK2. The alignment of the 611 VL sequence to the germline VK L6 sequence is shown in FIG. 3. Further analysis of the 611 VL sequence using the Kabat system of CDR region determination led to the delineation of the light chain CDR1, CDR2 and CD3 regions as shown in FIGS. 1B and 3, and in SEQ ID NOs: 4, 5 and 6, respectively.

To determine which heavy and light chain isotypes are utilized by antibody 611, the antibody was tested by ELISA. The ELISA plate was coated with goat anti-human kappa chain in 10 µg/ml PBS, 50 µl/well and incubated at 4° C. overnight. The plate was washed and blocked with 5% PBA (PBS containing 5% bovine serum albumin and 0.05% sodium azide), 150 µl/well and incubated at 37° C. for at least one hour. The plate was subsequently washed and supernatants from the fusion were added at 50-75 µl/well. The plates was incubated at 37° C. for 1-2 hours using PBA as a negative control and H22 (humanized anti-CD64 mAb) as a positive control at 10, 10.1 and 0.01 µg/ml. The plate was subsequently washed and alkaline phosphatase labeled anti-human gamma chain specific antibody or alkaline phosphatase labeled anti-human IgG1 was added at 50 µl/well. The plate was incubated 1-2 hours at 37° C. and washed. PNPP substrate at 1 mg/ml was added into the assay mix. OD's were read after color developed. The monoclonal antibody 611 was shown to express both human kappa light chain and human gamma heavy chain, and shown to be a human IgG1 antibody.

Example 3

Monoclonal Antibody 611 Binds Outside the IgG Ligand Binding Site on CD64

The monoclonal antibody 611 was tested for binding against IgG by a binding competition study using CD64-expressing U937 cells and flow cytometry (FACS analysis). CD64 expressing U937 cells were incubated with various concentration of FITC-labelled 611 (1 µg/ml), FITC-labeled H22 (humanized anti-CD64, 0.2 µg/ml), or FITC-labeled non-specific human IgG (0.1 µg/ml) for one hour on ice, in the presence of excess (3 mg/ml) unlabeled human IgG. The cells were washed and assessed for cell-associated fluorescence by flow cytometry using standard procedures.

HuMAb 611 binds to CD64 in the presence of human IgG, demonstrating that it binds outside the ligand binding site. The murine antibody H22 also binds outside the ligand binding site, but a nonspecific IgG does not. The results are shown in FIG. 4. Additionally, the assay was performed in the absence of IgG, and the HuMAb 611 was still able to bind to CD64 expressing U937 cells.

Example 4

Cross-Competition Studies with Murine and Humanized Anti-CD64 Monoclonal Antibodies Cross competition studies were performed as above using U937 cells and FACS analysis to compare binding between 611 and other monoclonal antibodies. CD64-expressing U937 cells were incubated with a fixed concentration of M32-FITC (Murine monoclonal anti-CD64 labeled with FITC, 2 µg/ml), 197-FITC (Murine monoclonal anti-CD64 labeled with FITC, 1 µg/ml) or 611-FITC (1 µg/ml), along with various concentrations of unlabeled H22, 611, or M32. The cells were washed and assessed for cell-associated fluorescence by flow cytometry. Unlabelled HuMAb 611 inhibits the binding of FITC-labeled antibody H22, M32, and M197 to CD64. Additionally, an assay was performed to test the effect of unlabeled antibody H22, M32, and M197 on the binding of FITC-labeled 611 to CD64. Each unlabelled antibody was capable of inhibiting the binding of FITC-labeled 611 to CD64 expressing U937 cells.

Example 5

Functional Activity of Human Monoclonal Antibodies to CD64

HuMAb 611 was tested, as described below, and shown to down-modulate CD64 surface expression and to inhibit CD64-mediated phagocytosis in a manner similar to the humanized anti-CD64 antibody, H22 (Graziano, R. F. et al. (1995) *J. Immunol.* 155 (10): 4996-5002 and PCT Publication WO 94/10332).

Figure 5:
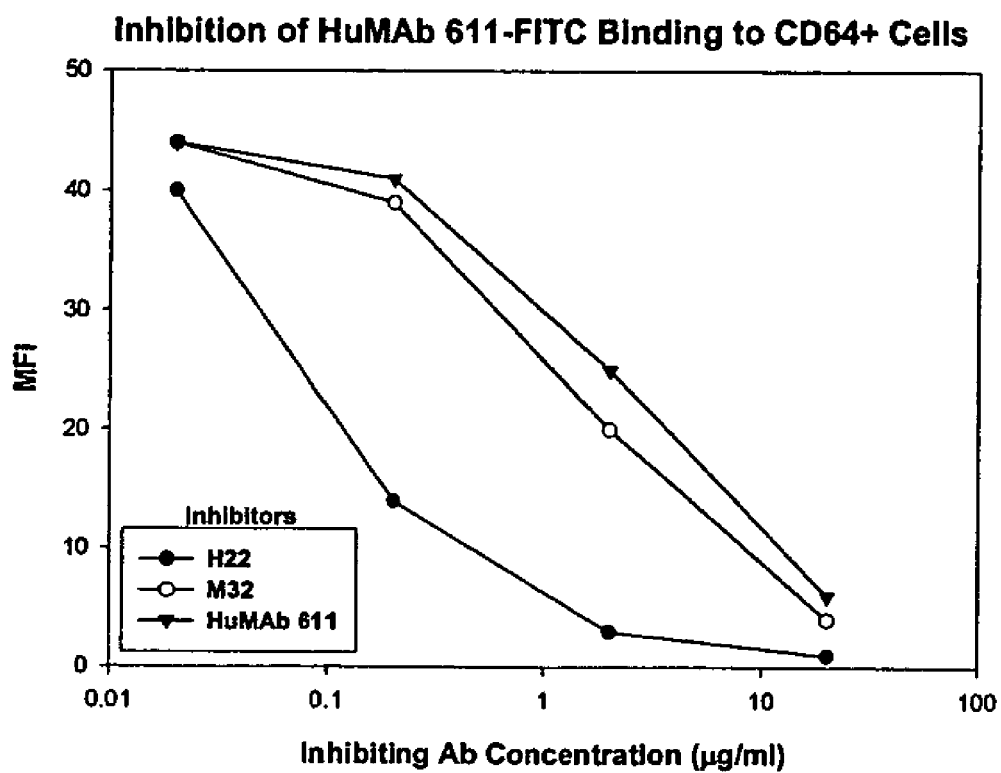
FIG. 5 is a graph showing that HuMAb 611 down-modulates CD64 surface expression on U937 cells.

For the surface modulation studies, CD64-expressing U937 cells were incubated with various concentrations of mAbs H22 or 611, either at 4° C. or at 37° C., for two hours. The cells were washed and incubated with FITC-labeled anti-human antibody. The cells were washed and assessed for cell-associated fluorescence by flow cytometry. The results are shown in FIG. 5. Percent (%) downmodulation of CD64 is a ratio of the amount fluorescence seen when the cells were incubated at 37° C. versus at 4° C.

Figure 6:
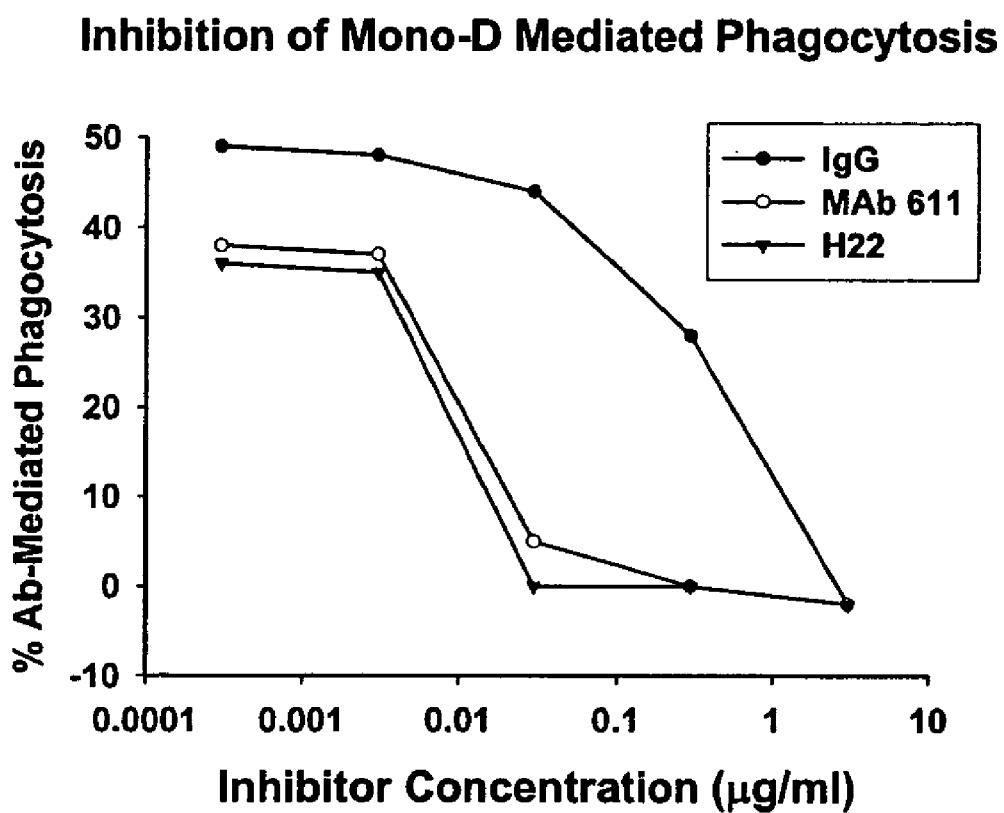
FIG. 6 is a graph showing that HuMAb 611 inhibits CD64-mediated phagocytosis.

The phagocytosis assay was conducted as described in Wallace, P. K. et al. (1997) *J. Leukocyte Biology* 62: 469-479. Briefly, a modified two-color flow cytometric assay was used to assess the effect of 611 on mono-D-mediated phagocytosis of red blood cells (RBC). Target RBC, collected in heparin by venipuncture from Rh-positive volunteers were labeled with PKH-24 (Sigma), a red fluorescent lipophilic dye that stably inserts into the cell membrane. Purified monocyte effector cells were resuspended in complete medium (CM) containing 10% fetal bovine serum and transferred to 96-well sterile polypropylene plates at a density of $5 \times 10^5$ effector cells per well in a volume of 200 µl. Monocytes were incubated in either CM alone as a control, or with 160 U of human rIFN-γ. After overnight incubation, monocyte effectors were washed twice to remove cytokine and resuspended in fresh CM. The anti-CD64 monoclonal antibody 611 was added to the monocytes. Mono-D (0.1 µg/ml) and PKH-26-labeled RBC (5:1 effector to target ratio) was added to make a final volume of 200 µl and the assay was incubated at 37° C. for 90 min. Phagocytosis was assayed by flow cytometry after labeling the monocytes with FITC-conjugated anti-CD14 Ab. CD14-positive monocytes were detected in the FU channel and PDH-26 positive RBC were detected in the FL2 channel. Phagocytosis was indicated by ingestion of the PKH-26-labeled target cell by a FITC-labeled effector. Mono-D-mediated phagocytosis was calculated by subtracting the percentage of nonspecific phagocytosis occurring in the absence of antibody from the total amount of phagocytosis occurring in the presence of Mono-D. The results are shown in FIG. 6. HuMAb 611 was shown to inhibit CD64-mediated phagocytosis in a manner similar to H22.

Example 6

Characterization of an Anti-CD64 Bispecific Antibody

Generation of Bispecific Antibody

A bispecific antibody, comprising an anti-CD64 antibody binding portion and a second antibody binding to a bacterial protein, was used to demonstrate the specific binding of the anti-CD64 antibody portion of the bispecific antibody to CD64 in a transgenic mouse model engineered to express human CD64.

Two HuMAb monoclonal antibodies, specifically the anti-CD64 antibody 611 and the anti-bacterial antibody 9A7, were used to generate a bispecific antibody. F(ab')$_2$ fragments of each of the HuMAbs were generated by pepsin digestion and purified to homogeneity by Superdex 200 gel filtration chromatography. Size exclusion HPLC was performed and both F(ab')$_2$ fragments were found to be >95% pure. Separate 611 and 9A7 Fab' fragments were then generated by mild reduction of the inter-heavy chain disulfide bonds of the F(ab')$_2$ fragment with mercaptoethanolamine (MEA). Size exclusion HPLC was performed and the 611 and 9A7 Fab' fragments were found to be >90% pure. The 611 and 9A7 Fab' fragments were separated from free MEA by G-25 column chromatography. The 611 Fab' fragment was incubated with dinitrothiobenzoate (DTNB) to generate a 611 Fab'-TNB conjugate. The 9A7 Fab' fragment and 611 Fab'-TNB conjugate were mixed at a 1:1 molar ratio overnight at room temperature. The resulting bispecific antibody was purified by Superdex 200 size exclusion chromatography.

Characterization of Binding Specificity of Bispecific Antibody

Figure 7:
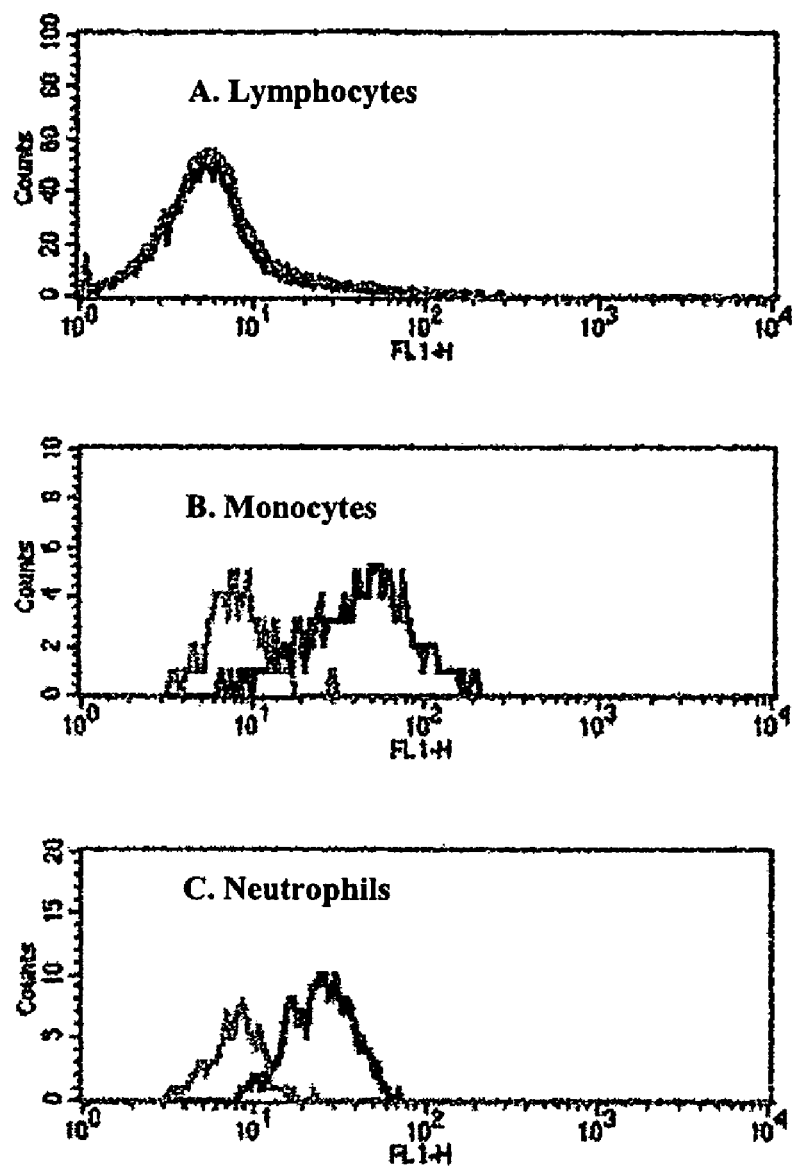
FIGS. 7A-7C are graphs showing the specific binding of an anti-CD64 bispecific antibody to monocytes (FIG. 7B) and neutrophils (FIG. 7C) from CD64-expressing human CD64 transgenic mice. Lymphocytes (FIG. 7A) are shown as a negative control.

The 611×9A7 bispecific antibody was used to test blood samples from human CD64 transgenic mice for binding to CD64 expressing cell types. Blood was taken from transgenic mice expressing a human CD64 transgene or from non-transgenic littermates. The blood was incubated with the bispecific antibodies at a concentration of 30 ug/ml for 30 minutes at room temperature. The blood was then washed and incubated with an FITC-labeled anti-human IgG antibody for 30 minutes at room temperature. The red blood cells were lysed and the remaining leukocytes were analyzed for staining by flow cytometry. Regions corresponding to the lymphocyte, monocyte, and neutrophil populations were gated and analyzed separately. The bispecific antibody comprising anti-human CD64 bound specifically to cells expressing human CD64. Human CD64 was shown to be expressed on monocytes and, to a lesser extent, neutrophils of human CD64 transgenic mice. Human CD64 was not expressed by the lymphocytes of the transgenic mice. The results are shown in FIG. 7.

This example demonstrates that a fully human antibody against human CD64 binds to CD64 on immune cells isolated from the blood of an animal engineered to express human CD64. The results confirm the specificity of the HuMAb for human CD64, and also validates this transgenic model for assessing efficacy of human CD64-directed therapeutics.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | SEQUENCE | SEQ ID NO: | SEQUENCE |
|---|---|---|---|
| 1 | VH CDR1 a.a. 611 | | |
| 2 | VH CDR2 a.a. 611 | | |
| 3 | VH CDR3 a.a. 611 | | |
| 4 | VK CDR1 a.a. 611 | | |
| 5 | VK CDR2 a.a. 611 | | |
| 6 | VK CDR3 a.a. 611 | | |
| 7 | VH a.a. 611 | | |
| 8 | VK a.a. 611 | | |
| 9 | VH n.t. 611 | | |
| 10 | VK n.t. 611 | | |
| 11 | VH 3-33 germline a.a. | | |
| 12 | VK L6 germline a.a. | | |

```

We claim:

1. An isolated monoclonal antibody, or antigen binding portion thereof, comprising:
   (a) heavy chain variable regions CDR1, CDR2, and CDR3 comprising the amino acid sequences of SEQ ID NO: 1, 2, and 3, respectively; and
   (b) light chain variable regions CDR1, CDR2, and CDR3 comprising the amino acid sequences of SEQ ID NO: 4, 5, and 6, respectively;
   wherein the antibody specifically binds to human CD64.

2. The antibody of claim 1, wherein the antibody exhibits at least one of the functional properties:
   (a) the antibody down-modulates CD64 surface expression;
   (b) the antibody does not block binding of CD64 to its natural ligand IgG;
   (c) the antibody inhibits CD64-mediated phagocytosis; or
   (d) the antibody mediates phagocytosis of target cells in the presence of human effector cells.

3. An isolated monoclonal antibody, or antigen binding portion thereof comprising:
   (a) a heavy chain variable region comprising the amino acid sequence of SEQ ID NO: 7; and
   (b) a light chain variable region comprising the amino acid sequence of SEQ ID NO: 8;
   wherein the antibody specifically binds to human CD64.

4. A composition comprising the antibody, or antigen-binding portion thereof, of claim 1 or 3, and a pharmaceutically acceptable carrier.

5. A hybridoma which produces the antibody of claim 1 or 3.

6. An isolated antibody, wherein the heavy chain variable region comprises the amino acid sequence set forth in SEQ ID NO:7, wherein the antibody specifically binds to human CD64.

7. An isolated antibody, wherein the light chain variable region comprises the amino acid sequence set forth in SEQ ID NO:8, wherein the antibody specifically binds to human CD64.

8. The antibody of claim 1, 3, 6, or 7, wherein the antibody is a human antibody.

* * * * *

                       SEQUENCE LISTING

<160> NUMBER OF SEQ ID NOS: 12

<210> SEQ ID NO 1
   <211> LENGTH: 5
   <212> TYPE: PRT
   <213> ORGANISM: Homo sapiens

<400> SEQUENCE: 1

Gly Tyr Gly Met His
   1               5

<210> SEQ ID NO 2
   <211> LENGTH: 17
   <212> TYPE: PRT
   <213> ORGANISM: Homo sapiens

<400> SEQUENCE: 2

Val Ile Trp Tyr Asp Gly Ser Asn Lys Tyr Tyr Ala Asp Ser Val Lys
   1               5                   10                  15

Gly

<210> SEQ ID NO 3
   <211> LENGTH: 9
   <212> TYPE: PRT
   <213> ORGANISM: Homo sapiens

<400> SEQUENCE: 3

Asp Thr Gly Asp Arg Phe Phe Asp Tyr
   1               5

<210> SEQ ID NO 4
   <211> LENGTH: 11
   <212> TYPE: PRT
   <213> ORGANISM: Homo sapiens

<400> SEQUENCE: 4

Arg Ala Ser Gln Ser Val Ser Ser Tyr Leu Ala
   1               5                   10

<210> SEQ ID NO 5
```

<211> LENGTH: 7
<212> TYPE: PRT
<213> ORGANISM: Homo sapiens

<400> SEQUENCE: 5

Asp Ala Ser Ser Arg Ala Thr
1               5

<210> SEQ ID NO 6
<211> LENGTH: 10
<212> TYPE: PRT
<213> ORGANISM: Homo sapiens

<400> SEQUENCE: 6

Gln Leu Arg Ser Asn Trp Pro Pro Tyr Thr
1               5                   10

<210> SEQ ID NO 7
<211> LENGTH: 118
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Gly Tyr
            20                  25                  30

Gly Met His Trp Val Arg Gln Ala Pro Gly Lys Gly Leu Glu Trp Val
        35                  40                  45

Thr Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Asp Arg Phe Phe Asp Tyr Trp Gly Gln Gly Thr
            100                 105                 110

Leu Val Thr Val Ser Ser
        115

<210> SEQ ID NO 8
<211> LENGTH: 108
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Gly Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Leu Arg Ser Asn Trp Pro Pro
                85                  90                  95

Tyr Thr Phe Gly Gln Gly Thr Lys Leu Glu Ile Lys
            100                 105

<210> SEQ ID NO 9
<211> LENGTH: 354
<212> TYPE: DNA
<213> ORGANISM: Homo sapiens
<220> FEATURE:
<221> NAME/KEY: CDS
<222> LOCATION: (1)..(354)

<400> SEQUENCE: 9

| cag gtg cag ctg gtg gag tct ggg gga ggc gtg gtc cag cct ggg agg | 48 |
|---|---|
| Gln Val Gln Leu Val Glu Ser Gly Gly Gly Val Val Gln Pro Gly Arg | |
| 1               5                  10                 15       | |

| tcc ctg aga ctc tcc tgt gca gcg tct gga ttc atc ttc agt ggc tat | 96 |
|---|---|
| Ser Leu Arg Leu Ser Cys Ala Ala Ser Gly Phe Ile Phe Ser Gly Tyr | |
|        20                  25                  30              | |

| ggc atg cac tgg gtc cgc cag gct cca ggc aag ggg ctg gag tgg gtg | 144 |
|---|---|
| Gly Met His Trp Val Arg Gln Ala Pro Gly Lys Gly Leu Glu Trp Val | |
|    35                  40                  45                  | |

| aca gtt ata tgg tat gat gga agt aat aaa tac tat gca gac tcc gtg | 192 |
|---|---|
| Thr Val Ile Trp Tyr Asp Gly Ser Asn Lys Tyr Tyr Ala Asp Ser Val | |
| 50                  55                  60                     | |

| aag ggc cga ttc acc atc tcc aga gac aat tcc aag aac acg ctg tat | 240 |
|---|---|
| Lys Gly Arg Phe Thr Ile Ser Arg Asp Asn Ser Lys Asn Thr Leu Tyr | |
| 65                  70                  75                  80 | |

| ctg caa atg aac agc ctg aga gcc gag gac acg gct gtg tat tac tgt | 288 |
|---|---|
| Leu Gln Met Asn Ser Leu Arg Ala Glu Asp Thr Ala Val Tyr Tyr Cys | |
|                 85                  90                  95     | |

| gcg aga gat acg ggg gat cgg ttc ttt gac tac tgg ggc cag gga acc | 336 |
|---|---|
| Ala Arg Asp Thr Gly Asp Arg Phe Phe Asp Tyr Trp Gly Gln Gly Thr | |
|             100                 105                 110        | |

| ctg gtc acc gtc tcc tca | 354 |
|---|---|
| Leu Val Thr Val Ser Ser | |
|         115             | |

<210> SEQ ID NO 10
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 10

| gaa att gtg ttg aca cag tct cca gcc acc ctg tct ttg tct cct ggg | 48 |
|---|---|
| Glu Ile Val Leu Thr Gln Ser Pro Ala Thr Leu Ser Leu Ser Pro Gly | |
| 1               5                  10                 15       | |

| gaa aga gcc acc ctc tcc tgc agg gcc agt caa agt gtt agc agc tac | 96 |
|---|---|
| Glu Arg Ala Thr Leu Ser Cys Arg Ala Ser Gln Ser Val Ser Ser Tyr | |
|        20                  25                  30              | |

| tta gcc tgg tac caa cag aaa cct ggc cag gct ccc agg ctc ctc atc | 144 |
|---|---|
| Leu Ala Trp Tyr Gln Gln Lys Pro Gly Gln Ala Pro Arg Leu Leu Ile | |
|    35                  40                  45                  | |

| tat gat gca tcc agc agg gcc act ggc atc cca gcc agg ttc ggt ggc | 192 |
|---|---|
| Tyr Asp Ala Ser Ser Arg Ala Thr Gly Ile Pro Ala Arg Phe Gly Gly | |
| 50                  55                  60                     | |

| agt ggg tct ggg aca gac ttc act ctc acc atc agc agc cta gag cct | 240 |
|---|---|
| Ser Gly Ser Gly Thr Asp Phe Thr Leu Thr Ile Ser Ser Leu Glu Pro | |
| 65                  70                  75                  80 | |

| gaa gat ttt gca gtt tat tac tgt cag ctg cgt agc aac tgg cct ccg | 288 |
|---|---|
| Glu Asp Phe Ala Val Tyr Tyr Cys Gln Leu Arg Ser Asn Trp Pro Pro | |
|                 85                  90                  95     | |

```
tac act ttt ggc cag ggg acc aag ctg gag atc aaa                    324
Tyr Thr Phe Gly Gln Gly Thr Lys Leu Glu Ile Lys
            100                 105

<210> SEQ ID NO 11
<211> LENGTH: 98
<212> TYPE: PRT
<213> ORGANISM: Homo sapiens

<400> SEQUENCE: 11

Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 12
<211> LENGTH: 94
<212> TYPE: PRT
<213> ORGANISM: Homo sapiens

<400> SEQUENCE: 12

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp
                 85                  90
```